US009186276B2

United States Patent
Parziale

(10) Patent No.: US 9,186,276 B2
(45) Date of Patent: Nov. 17, 2015

(54) TRAVEL SLEEP MASK APPARATUS TO SUPPORT THE HEAD OF A USER

(71) Applicant: Thomas Parziale, Los Angeles, CA (US)

(72) Inventor: Thomas Parziale, Los Angeles, CA (US)

( * ) Notice: Subject to any disclaimer, the term of this patent is extended or adjusted under 35 U.S.C. 154(b) by 0 days.

(21) Appl. No.: 14/495,191

(22) Filed: Sep. 24, 2014

(65) Prior Publication Data
US 2015/0082515 A1    Mar. 26, 2015

Related U.S. Application Data

(60) Provisional application No. 61/881,538, filed on Sep. 24, 2013.

(51) Int. Cl.
*A61F 9/04* (2006.01)
*A47C 7/38* (2006.01)

(52) U.S. Cl.
CPC .. *A61F 9/04* (2013.01); *A47C 7/383* (2013.01)

(58) Field of Classification Search
CPC .......... A42B 1/046; A42B 3/20; B63C 11/04; A41D 13/0512; A47G 9/10; A47G 9/1045
USPC ................ 2/173, 9, 15, 468; 5/636, 639, 640; 132/319
See application file for complete search history.

(56) References Cited

U.S. PATENT DOCUMENTS

| | | | |
|---|---|---|---|
| 1,924,315 A * | 8/1933 | Hemphill et al. | 2/15 |
| 2,191,937 A * | 2/1940 | Low | 2/12 |
| 3,541,608 A | 11/1970 | Otwell | |
| 5,184,354 A * | 2/1993 | Alfaro et al. | 2/425 |
| 6,293,900 B1 * | 9/2001 | Bove et al. | 600/15 |
| 6,543,056 B2 | 4/2003 | Spiteri | |
| 6,607,245 B1 | 8/2003 | Scher | |
| 6,651,256 B1 * | 11/2003 | Swift | A42B 1/004 2/15 |
| 6,748,615 B1 * | 6/2004 | Tiedemann | 5/640 |
| 6,817,068 B2 | 11/2004 | Cleary | |
| 8,239,987 B2 * | 8/2012 | Sharp | 5/639 |
| D694,309 S | 11/2013 | Shelledy | |
| 2007/0180623 A1 | 8/2007 | Stein et al. | |
| 2012/0210516 A1 | 8/2012 | Popovic | |
| 2014/0041091 A1 | 2/2014 | Sternlight | |

OTHER PUBLICATIONS

International Search Report dated Dec. 5, 2014 from corresponding international application PCT/US2014/057294 USPTO PCT Division.

* cited by examiner

*Primary Examiner* — Tejash Patel
(74) *Attorney, Agent, or Firm* — Plager Schack LLP

(57) ABSTRACT

A support mask apparatus secured to a head of a user and a supporting structure to enhance sleep quality by supporting the head in a stationary and neutral position is provided. The support mask includes an opaque protective member placed over eyes of the user, an elastic strap with a first end coupled to a left edge of the protective member and a second end coupled to a right edge of the protective member, the elastic strap able to be secured around the head of the user, a flexible cord with a first end coupled to the left edge of the protective member and a second end coupled to the right edge of the protective member, and an adjustment mechanism operably connected to the flexible cord. The adjustment mechanism enables the user to securely fasten the flexible cord around the supporting structure.

5 Claims, 4 Drawing Sheets

TRAVEL SLEEP MASK APPARATUS TO SUPPORT THE HEAD OF A USER

RELATED APPLICATION

The application claims priority to provisional patent application U.S. Ser. No. 61/881,538 filed on Sep. 24, 2013, the entire contents of which is herein incorporated by reference.

BACKGROUND

The embodiments herein relate generally to eye masks or sleep masks used by individuals to enhance sleep quality.

Individuals often wear sleep masks over their eyes to improve sleep quality in bright light locations. One common problem faced by these individuals is the diminished sleep quality experienced when traveling on moving vehicles such as airplanes, automobiles, trains, or the like. Motion of these vehicles causes the individual's head to sway side to side, up and down. This prevents the individual from falling asleep and/or negatively affects sleep quality. This motion causes the individual's head to deviate from a neutrally aligned position, thereby causing the individual to suffer neck pain and/or injuries.

Several head restraint masks exist to secure a user's head to a seat such as U.S. Pat. Nos. 6,607,245 and 8,239,987, and U.S. Patent Application Publication 2014/0041091. However, these head restraint masks are difficult and/or awkward to use because they comprise bulky components or are not easily adjusted. Further, due to the bulky design, individuals may be unwilling to use these masks on a public vehicle due to the fear of being embarrassed.

As such, there is a need in the industry for a travel support sleep mask apparatus that effectively secures the user's head in a stationary position and addresses the limitations of the prior art.

SUMMARY

A support mask apparatus configured to be secured to a head of a user and a supporting structure to enhance sleep quality by supporting the head in a stationary and neutral position is provided. The support mask comprises an opaque protective member configured to be placed over eyes of the user, an elastic strap comprising a first end coupled to a left edge of the protective member and a second end coupled to a right edge of the protective member, the elastic strap configured to be secured around the head of the user, a flexible cord comprising a first end coupled to the left edge of the protective member and a second end coupled to the right edge of the protective member, and an adjustment mechanism operably connected to the flexible cord, wherein the adjustment mechanism is configured to enable the user to securely fasten the flexible cord around the supporting structure.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
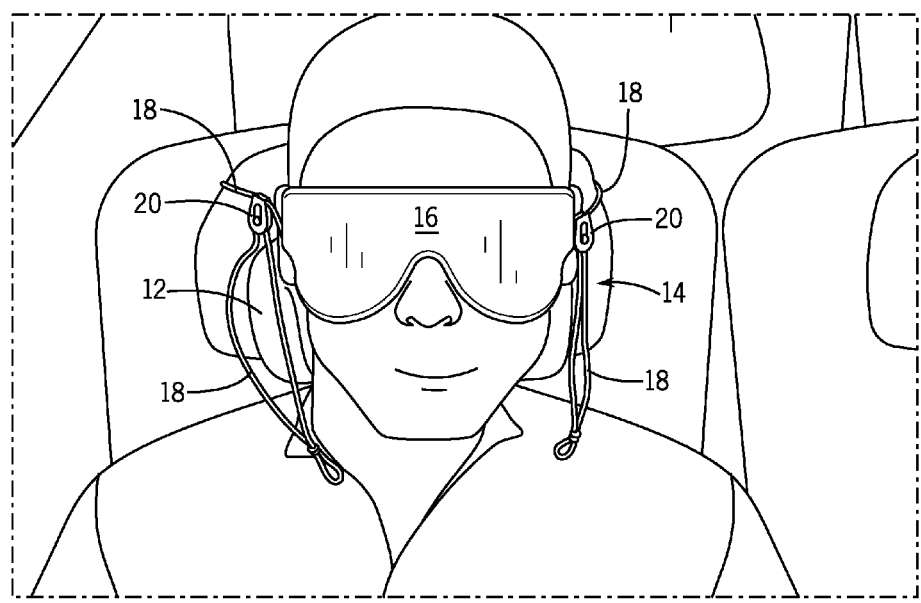
FIG. 1 depicts a front elevation view of certain embodiments of the support mask apparatus shown in use.
Figure 2:
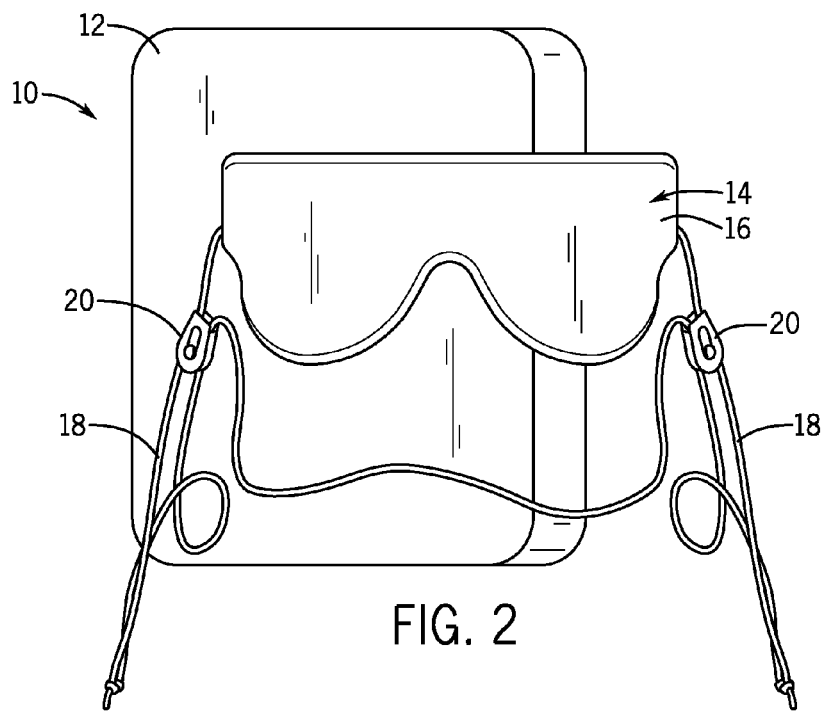
FIG. 2 depicts a front elevation view of certain embodiments of the support mask apparatus.
Figure 3:
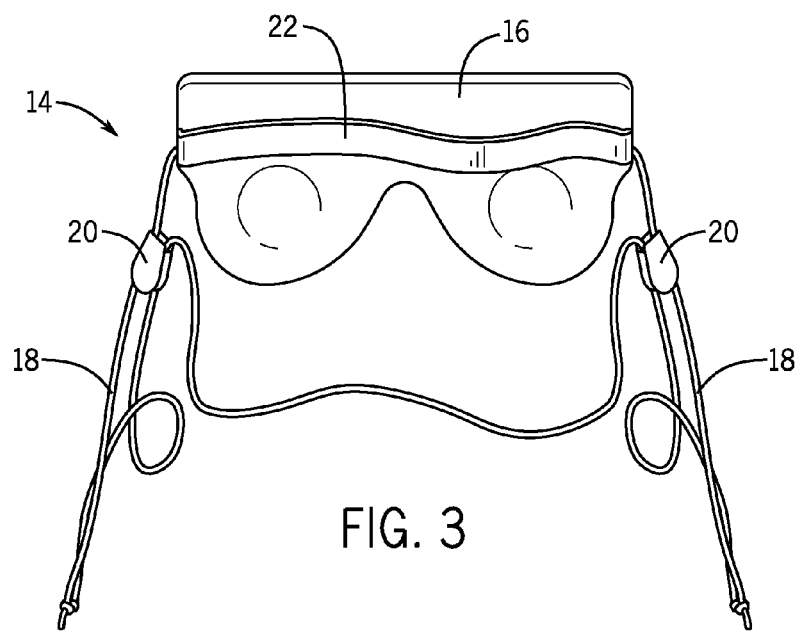
FIG. 3 depicts a rear elevation view of certain embodiments of the support mask apparatus.

As depicted in FIGS. 1-3, support mask apparatus 10 is configured for use on a user and a supporting structure such as a headrest or backrest of a seat on an airplane, train, bus, car, other vehicle, or the like. However, it shall be appreciated that support mask apparatus 10 can be used on any other seat in any location such as a home, business, airport, waiting room, or the like. Support mask apparatus 10 comprises mask unit 14 and pillow 12.

Mask 16 comprises an opaque protective member with approximate dimensions of 9.5"×4". The opaque protective member comprises an inner foam layer surrounded by an outer fabric layer. The inner foam layer may comprise polyurethane foam, memory foam, or the like. The outer fabric layer is made from pima cotton, spandex, a rayon blend, or any other material or combination of materials known in the field. Elastic strap 22 comprises a first end coupled to a left edge of mask 16 and a second end coupled to a right edge of mask 16. Any fastening components known in the field may be used such as stitching, snap components, hook and loop fasteners, or the like. In a preferred embodiment, elastic strap 22 comprises a ½" width with a variable length.

Flexible cord 18 comprises a first end coupled to a left edge of mask 16 and a second end coupled to a right edge of mask 16. In a preferred embodiment, flexible cord 18 comprises a 58 inch length and 0.375" diameter. However, flexible cord 18 may have alternative dimensions. The cord may be made from any material known in the field. A pair of toggles 20 is operably connected to flexible cord 18. Toggles 20 enable the user to adjust the flexible cord 18 loop size to enable the loop to be securely fastened such that the cord conforms around the user's head and seat headrest as depicted in FIG. 1. Alternative adjustment mechanisms can be used instead of toggles such as "o" or "s" rings, snaps, buckles, or the like.

Figure 4:
FIG. 4 depicts a perspective view of certain embodiments of the support mask apparatus depicting pillow 12.

Pillow 12 comprises a substantially rectangular shape and is configured to be placed between the user's neck and headrest as depicted in FIG. 4. In a preferred embodiment, pillow 12 has approximate dimensions of 12"×8"×2" and is made from the same materials as mask 16. This provides the user's neck and head with additional support and stability when seated. Typically, pillow 12 will be folded prior to being used. The user may find that any number of folds may be required to provide the neck support desired. In one embodiment, pillow 12 comprises an opening to store mask 16, flexible cord 18 and elastic strap 22 when not in use.

To operate support mask apparatus 10, mask 16 is placed over the user's eyes and elastic strap 22 is secured around the user's head. The loop of flexible cord 18 is placed around the user's head and the supporting structure such as a seat headrest. Toggles 20 are adjusted such that the loop of flexible cord 18 conforms around the user's head and the seat headrest to a secured position. Pillow 12 is folded and placed between the user's head and the seat headrest. As depicted in FIG. 1, this configuration secures the user's head in a stationary and comfortable position. More specifically, the user's head and neck remain in a neutrally aligned position, which enhances sleep quality and minimizes the risk of injury to the user.

Figure 5:
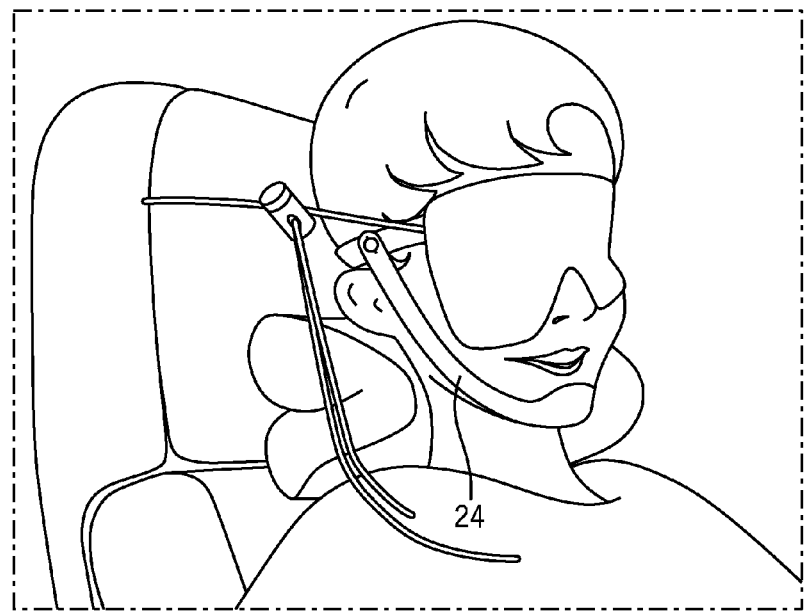
FIG. 5 depicts a perspective view of certain embodiments of the support mask apparatus depicting chin strap 24.

As depicted in FIG. 5, chin strap 24 is affixed to elastic strap 22 by any fastening components known in the field. Chin strap 24 is configured to be placed under the chin of the user once elastic band 22 and flexible cord 18 are properly adjusted. Chin strap 24 keeps the user's jaw closed when sleeping and prevents any saliva from flowing out of the user's mouth. Chin strap 24 is configured to be easily attached to and removed from elastic band 22.

Figure 6:
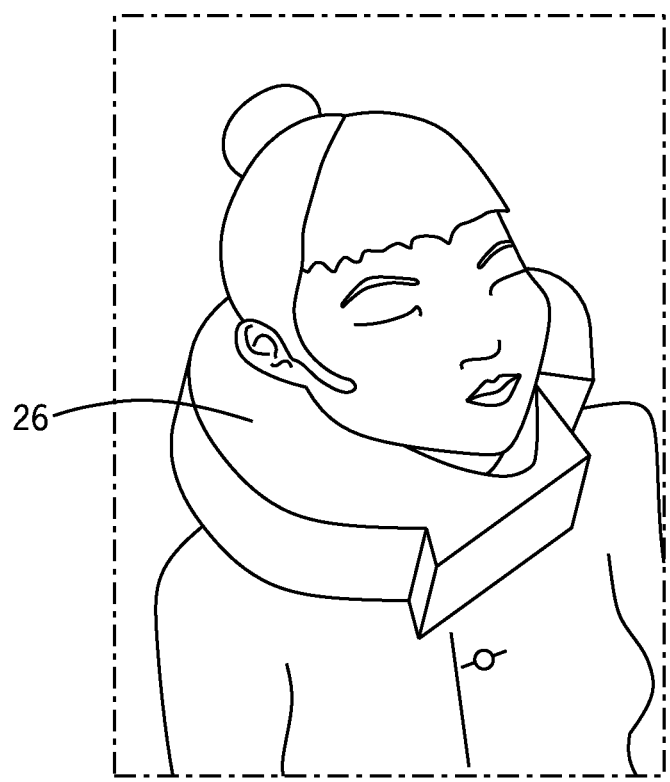
FIG. 6 depicts a perspective view of certain embodiments of the support mask apparatus depicting G-shaped pillow 26.

In an alternative embodiment, G-shaped pillow 26 may be used instead of pillow 12 as depicted in FIG. 6. G-shaped pillow 26 may be made from the same materials as pillow 12 and have variable dimensions. G-shaped pillow 26 provides enhanced neck and head support to the user when secured around the user's neck. The bottom interior portion of G-shaped pillow 26 comprises a concave portion that is designed to fit the contours of the user's chin. It shall be appreciated that G-shaped pillow 26 may be used by itself or together with support mask apparatus 10.

It shall be appreciated that the components of support mask apparatus 10 described in several embodiments herein may comprise any alternative known materials in the field and be of any color, size and/or dimensions. This allows the apparatus to be used by users of all ages including, infants, children and adults. It shall be appreciated that the components of support mask apparatus 10 described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A support kit configured to be secured to a user to enhance sleep quality by supporting a head of a user in a stationary and neutral position, the support kit comprising a mask disposed around the head of the user and a supporting structure, and a support pillow disposed around a neck of the user, the support kit consisting essentially of:
   an opaque protective member configured to be placed over eyes of the user;
   an elastic strap comprising a first end coupled to a left edge of the protective member and a second end coupled to a right edge of the protective member, the elastic strap configured to be secured around the head of the user;
   a flexible cord comprising a first end coupled to the left edge of the protective member and a second end coupled to the right edge of the protective member;
   an adjustment mechanism operably connected to the flexible cord, wherein the adjustment mechanism is configured to enable the user to securely fasten the flexible cord around the supporting structure; and
   a G-shaped pillow secured around the neck of the user and comprising a top portion and a bottom portion, the bottom portion comprising an interior concave portion configured to conform to contours of a chin of the user, thereby enhancing support of the neck and head.

2. The support mask apparatus of claim 1, wherein the adjustment mechanism comprises a pair of toggles operably connected to the flexible cord.

3. The support mask apparatus of claim 2, further comprising an elastic chin strap coupled to the elastic strap, wherein the chin strap is configured to be secured around a chin of the user.

4. The support mask apparatus of claim 2, further comprising a rectangular pillow disposed between the neck of the user and the supporting structure.

5. The support mask apparatus of claim 4, wherein the rectangular pillow comprises an opening, wherein the rectangular pillow is configured to store the opaque protective member, the elastic strap, the flexible cord and adjustment mechanism within the pillow opening.

* * * * *